(12) United States Patent
Malyugin et al.

(10) Patent No.: US 10,537,473 B2
(45) Date of Patent: *Jan. 21, 2020

(54) IMPLANTATION ASSEMBLY FOR AN IRIS-EXPANDING DEVICE

(71) Applicants: Boris Malyugin, Moscow (RU); MicroSurgical Technology, Inc., Redmond, WA (US)

(72) Inventors: Boris Malyugin, Moscow (RU); Vaclav Dusek, Bellevue, WA (US); Lawrence Laks, Bellevue, WA (US)

(73) Assignee: Microsurgical Technology, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/981,639

(22) Filed: May 16, 2018

(65) Prior Publication Data

US 2018/0333301 A1 Nov. 22, 2018

Related U.S. Application Data

(63) Continuation of application No. 15/648,360, filed on Jul. 12, 2017, now Pat. No. 9,980,852, which is a (Continued)

(51) Int. Cl.
*A61F 9/007* (2006.01)
*A61B 17/02* (2006.01)
*A61F 9/00* (2006.01)

(52) U.S. Cl.
CPC ...... *A61F 9/00736* (2013.01); *A61B 17/0231* (2013.01); *A61F 9/0017* (2013.01)

(58) Field of Classification Search
CPC ...... A61F 9/00736; A61F 9/0017; A61F 2/14; A61F 2/1662; A61F 2250/001;
(Continued)

(56) References Cited

U.S. PATENT DOCUMENTS

| | | |
|---|---|---|
| 1,506,186 A | 8/1924 | Owen et al. |
| 2,761,457 A | 9/1956 | Wood |

(Continued)

FOREIGN PATENT DOCUMENTS

| | | |
|---|---|---|
| DE | 93 20 127 U1 | 4/1994 |
| RU | 14506 U1 | 2/2000 |

(Continued)

OTHER PUBLICATIONS

Cimberle, M., "New Pupil Expander Easier to Implant, Gentle on the Iris," *Ocular Surgery News Europe Asia Edition*, [online], May 2006 [retrieved on Mar. 27, 2013]. Retrieved from the Internet URL: hap://www.osasupersite.com/view.aspx?rid-16863.

(Continued)

*Primary Examiner* — Paul B Prebilic
(74) *Attorney, Agent, or Firm* — Hamilton, Brook, Smith & Reynolds, P.C.

(57) ABSTRACT

An iris-expanding device injector assembly is described. The iris-expanding device injector assembly has a handle, a slider and/or button coupled with the handle and configured to slide with respect to the handle, a cannula coupled with the handle, the cannula configured to slide in to and out from a holder containing an iris-expanding device, and a hook housed within the cannula.

20 Claims, 4 Drawing Sheets

Related U.S. Application Data continuation of application No. 13/661,982, filed on Oct. 26, 2012, which is a continuation of application No. 12/074,742, filed on Mar. 5, 2008, now Pat. No. 8,323,296.

(60) Provisional application No. 60/918,405, filed on Mar. 15, 2007.

(58) Field of Classification Search
CPC ...... A61F 2250/0008; A61F 2250/0059; A61F 2250/006; A61F 2250/0065; A61F 2250/006; A61F 2250/0007; A61F 2250/0004; A61B 17/0231
See application file for complete search history.

(56) References Cited

U.S. PATENT DOCUMENTS

| | | | |
|---|---|---|---|
| 3,975,779 A | 8/1976 | Richards et al. | |
| 4,203,168 A | 5/1980 | Rainin et al. | |
| 4,321,916 A | 3/1982 | McKee | |
| 4,387,706 A | 6/1983 | Glass | |
| 4,412,532 A | 11/1983 | Anthony | |
| 4,446,582 A | 5/1984 | Hanna | |
| 4,782,820 A | 11/1988 | Woods | |
| 4,991,567 A | 2/1991 | McCuen et al. | |
| 5,163,419 A | 11/1992 | Goldman | |
| 5,267,553 A | 12/1993 | Graether | |
| 5,299,564 A | 4/1994 | Sabatino | |
| 5,318,011 A | 6/1994 | Federman et al. | |
| 5,322,054 A | 6/1994 | Graether | |
| 5,334,217 A | 8/1994 | Das | |
| 5,374,272 A | 12/1994 | Arpa et al. | |
| 5,427,088 A | 6/1995 | Graether | |
| 5,441,045 A | 8/1995 | Federman | |
| 5,456,274 A | 10/1995 | Selbee et al. | |
| 5,489,295 A | 2/1996 | Piplani et al. | |
| 5,634,884 A | 6/1997 | Graether | |
| 5,693,085 A | 12/1997 | Buirge et al. | |
| 5,951,565 A | 9/1999 | Freeman | |
| 6,068,643 A | 5/2000 | Milverton | |
| 6,200,336 B1 | 3/2001 | Pavcnik et al. | |
| 6,231,583 B1 | 5/2001 | Lee | |
| 6,332,866 B1 | 12/2001 | Grieshaber | |
| 6,497,724 B1 | 12/2002 | Stevens et al. | |
| 6,620,098 B1 | 9/2003 | Milverton | |
| 6,814,748 B1 | 11/2004 | Baker et al. | |
| 7,305,996 B2 | 12/2007 | Kraft et al. | |
| 7,412,993 B2 | 8/2008 | Tzeng | |
| 7,985,180 B2 | 7/2011 | Brown | |
| 8,257,256 B1 | 9/2012 | Krolman | |
| 8,323,296 B2 | 12/2012 | Malyugin | |
| 8,376,743 B1 | 2/2013 | Bukhary | |
| 8,439,833 B2 * | 5/2013 | Christensen | A61B 17/0231 600/236 |
| 8,496,583 B1 | 7/2013 | Reynard | |
| 8,900,136 B2 | 12/2014 | Cote et al. | |
| 9,089,397 B2 | 7/2015 | Clarke | |
| 9,504,459 B1 | 11/2016 | Nallakrishnan | |
| 9,763,653 B2 | 9/2017 | Malyugin | |
| 9,917,710 B2 | 3/2018 | Malyugin et al. | |
| 9,918,710 B2 | 3/2018 | Malyugin et al. | |
| 9,974,688 B2 | 5/2018 | Malyugin et al. | |
| 9,980,852 B2 | 5/2018 | Malyugin et al. | |
| 2002/0004676 A1 | 1/2002 | Wallace | |
| 2002/0120277 A1 * | 8/2002 | Hauschild | A61B 17/221 606/108 |
| 2003/0092970 A1 | 5/2003 | Lee | |
| 2005/0192606 A1 | 9/2005 | Paul et al. | |
| 2007/0239141 A1 | 10/2007 | Hartley | |
| 2008/0108879 A1 | 5/2008 | Brown | |
| 2008/0243139 A1 | 10/2008 | Dusek | |
| 2008/0262592 A1 | 10/2008 | Jordan | |
| 2008/0269888 A1 | 10/2008 | Malyugin | |
| 2008/0275461 A1 | 11/2008 | Nallakrishnan | |
| 2009/0259260 A1 * | 10/2009 | Bentley | A61B 17/0057 606/300 |
| 2010/0274257 A1 * | 10/2010 | Neusidl | A61F 9/0017 606/107 |
| 2012/0136322 A1 | 5/2012 | Alster et al. | |
| 2012/0289786 A1 | 11/2012 | Dusek | |
| 2013/0053860 A1 | 2/2013 | Malyugin | |
| 2013/0096386 A1 | 4/2013 | Christensen et al. | |
| 2013/0131458 A1 | 5/2013 | Malugin et al. | |
| 2013/0267988 A1 | 10/2013 | Sussman et al. | |
| 2013/0331939 A1 | 12/2013 | Stevens | |
| 2014/0221759 A1 | 8/2014 | Mackool et al. | |
| 2014/0378773 A1 | 12/2014 | Dykes | |
| 2015/0164685 A1 | 6/2015 | Bhattacharjee | |
| 2015/0265269 A1 | 9/2015 | Malyugin | |
| 2017/0265851 A1 | 9/2017 | Kahook et al. | |
| 2017/0312126 A1 | 11/2017 | Malyugin et al. | |
| 2017/0312127 A1 | 11/2017 | Malyugin et al. | |
| 2018/0303474 A1 | 10/2018 | Malyugin et al. | |

FOREIGN PATENT DOCUMENTS

| | | |
|---|---|---|
| RU | 14505 U1 | 9/2000 |
| WO | WO 95/15120 | 6/1995 |
| WO | WO 00/32141 | 6/2000 |
| WO | WO 2008/115454 A1 | 9/2008 |
| WO | WO 2008/115455 A1 | 9/2008 |

OTHER PUBLICATIONS

He et al, "Distribution and Heritability of Iris Thickness and Pupil Size in Chinese: The Guangzhou Twin Eye Study", Apr. 2009, IOVS ARVO Journal, vol. 50, Issue 4, pp. 1593-1597.

Written Opinion of the International Searching Authority dated Jul. 23, 2008 for International Application No. PCT/US2008/003472, entitled "Ring Used in a Small Pupil Phacoemulsification Procedure".

International Preliminary Report on Patentability dated Sep. 15, 2009 for International Application No. PCT/US2008/003472,entitled "Ring Used in a Small Pupil Phacoemulsification Procedure".

* cited by examiner

IMPLANTATION ASSEMBLY FOR AN IRIS-EXPANDING DEVICE

RELATED APPLICATIONS

This application is a continuation of U.S. application Ser. No. 15/648,360 filed on Jul. 12, 2017, now U.S. Pat. No. 9,980,852 issued May 29, 2018, which is a continuation of Ser. No. 13/661,982 filed Oct. 26, 2012, which is a continuation of U.S. application Ser. No. 12/074,742, filed Mar. 5, 2008, now U.S. Pat. No. 8,323,296 issued Dec. 4, 2012, which claims the benefit of U.S. Provisional Application No. 60/918,405 filed on Mar. 15, 2007.

The entire teachings of the above application(s) are incorporated herein by reference.

BACKGROUND OF THE INVENTION

Field of the Invention

The present invention relates to a ring used in an ophthalmic surgical procedure.

Background Information

There are various ophthalmic procedures that require the dilation of the pupil. For example, cataracteous lenses are typically replaced in a procedure commonly referred to as phacoemulsification or phaco for short. In a phaco procedure the lens is broken up with an instrument, typically with an ultrasonically driven tool. The instrument has an aspiration port that aspirates the broken lens material from the patient's ocular chamber.

It is desirable to extend the pupil during a phaco procedure to provide the surgeon with a wide view of the lens. One technique for extending the pupil includes pulling back the iris with a series of plastic hooks. It is has been found that using plastic hooks can cause damage to iris tissue.

SUMMARY OF THE INVENTION

A ring used to maintain a pupil in an extended position during an ophthalmic procedure. The ring has a plurality of loops.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Described is a ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

Figure 1:
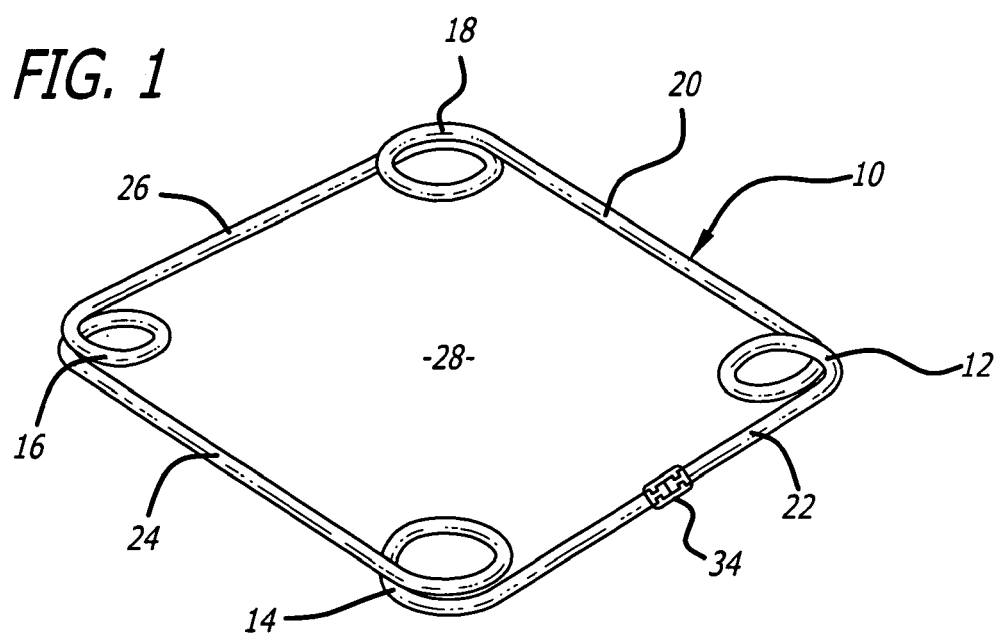
FIG. 1 is an illustration of a ring of the present invention.

Referring to the drawings more particularly by reference numbers, FIG. 1 shows an embodiment of a ring 10 that can be used to extend a pupil during an ophthalmic procedure. The ring 10 has a plurality of loops 12, 14, 16 and 18 located at the corners of four sides 20, 22, 24 and 26. Each loop 12, 14, 16 and 18 may be formed by one full turn. Although one full turn is shown and described, it is to be understood that each loop 12, 14, 16 and 18 may have multiple turns. The four sides 20, 22, 24 and 26 circumscribe a center opening 28.

The ring 10 preferably has a square configuration such that the sides 20, 22, 24 and 26 are of equal dimension. Although a square ring is shown and described, it is to be understood that the ring may have a rectangular configuration where all sides 20, 22, 24 and 26 are not of equal dimension. Additionally, the ring may have a nonrectangular shape. For example, the ring 10 may be shaped as a triangle that has three sides and three loops located at the ring corners. Although three and four sided rings have been described, it is to be understood that the ring may have any number of side and loops. The ring 10 is preferably constructed from a molded plastic material, although it is to be understood that other materials such as metal or plastic coated metal may be employed.

Figure 2:
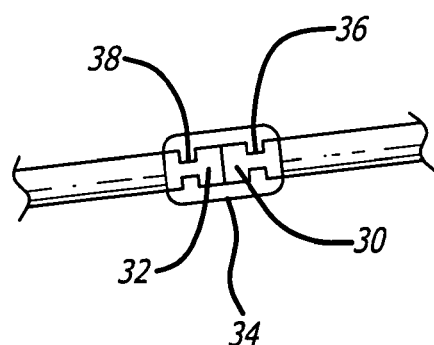
FIG. 2 is an illustration showing an enlarged view of the ring.

FIG. 2 shows a preferred embodiment for constructing the ring 10. One side 20 of the ring 10 has two ends 30 and 32 that are butt attached by an adhesive 34. Each end 30 and 32 may have an indent 36 and 38, respectively. The adhesive 34 can flow into the indents 36 and 38 to increase the strength of the butt attachment of the ring 10. The indents 36 and 38 create surface structure that minimizes shearing and delamination of the adhesive 34 from the ring 10. By way of example, the adhesive 34 may be a biocompatible material such as Class VI epoxy. The adhesive 34 can be applied with a tool (not shown) that insures a repeatable volume and dimensions of the solidified adhesive form.

Figure 3:
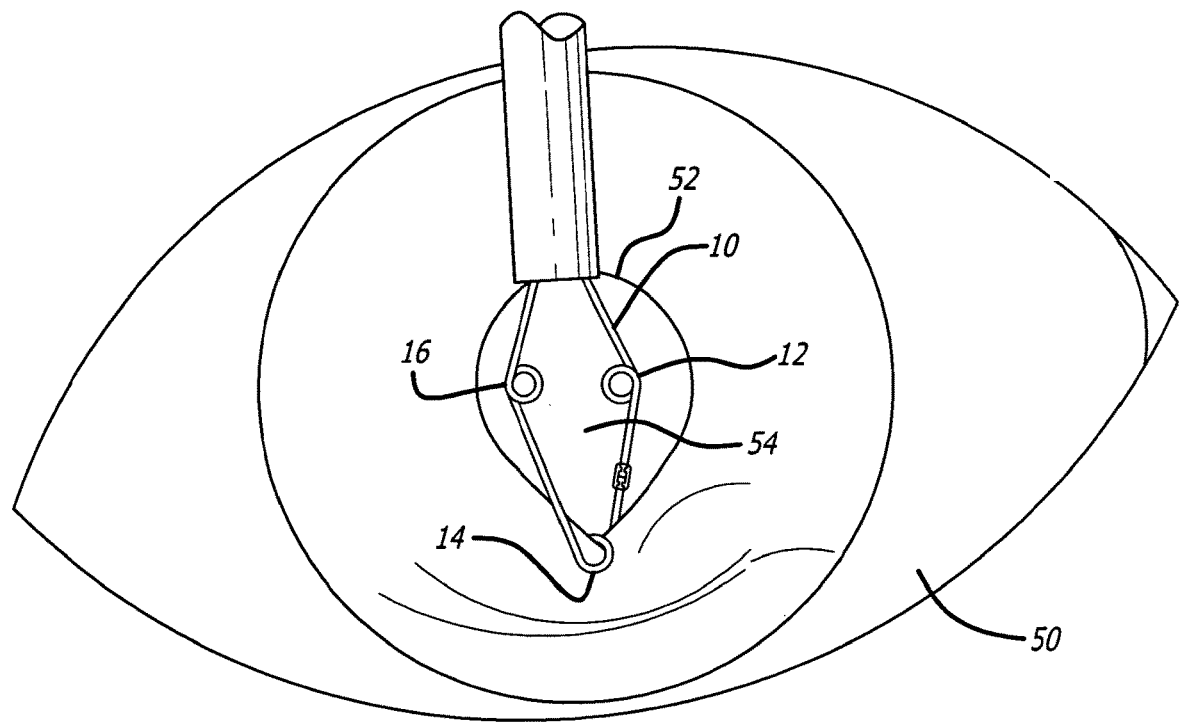
FIG. 3 is an illustration showing iris tissue being inserted into a first loop of the ring.
Figure 4:
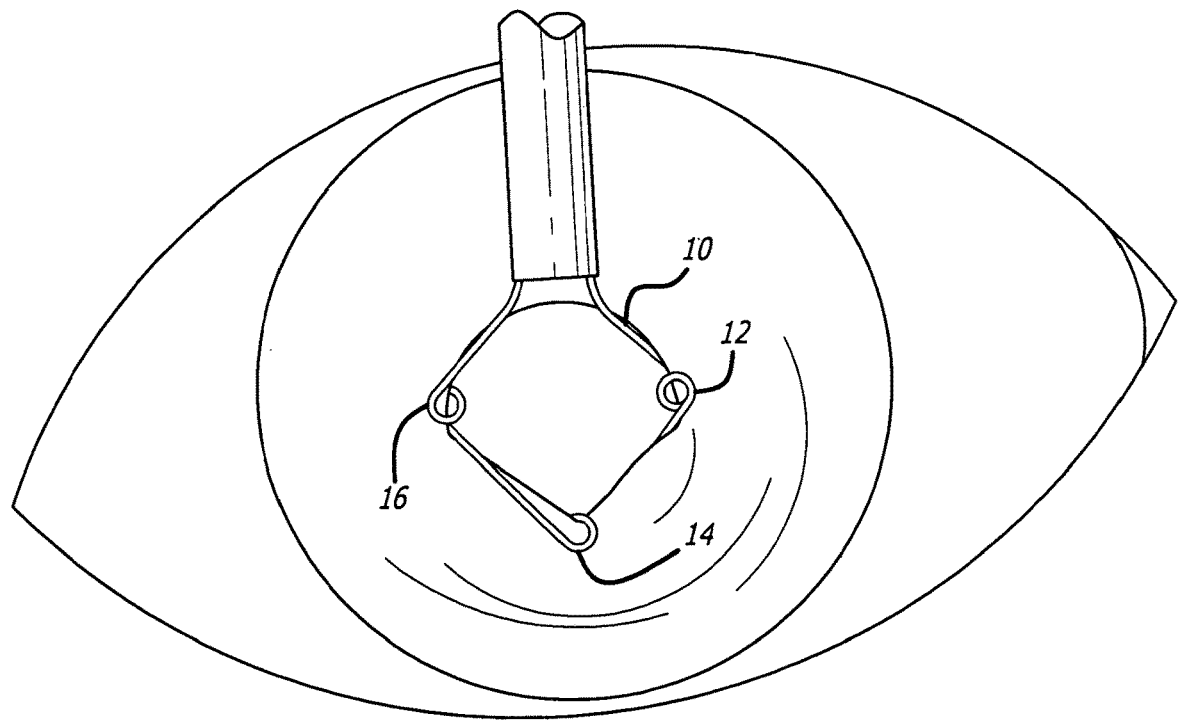
FIG. 4 is an illustration showing iris tissue being inserted into a second loop of the ring.

FIG. 3 shows the initial stages of the ring 10 being inserted into a patient's eye 50 to stretch the iris 52 and extend the pupil 54. A tool such as a forcep (not shown) can be used to pull the iris so that iris tissue is inserted into loop 14 of the ring 10. As shown in FIG. 4, the ring 10 can be manipulated so that iris tissue is inserted into loops 12 and 16.

Figure 5:
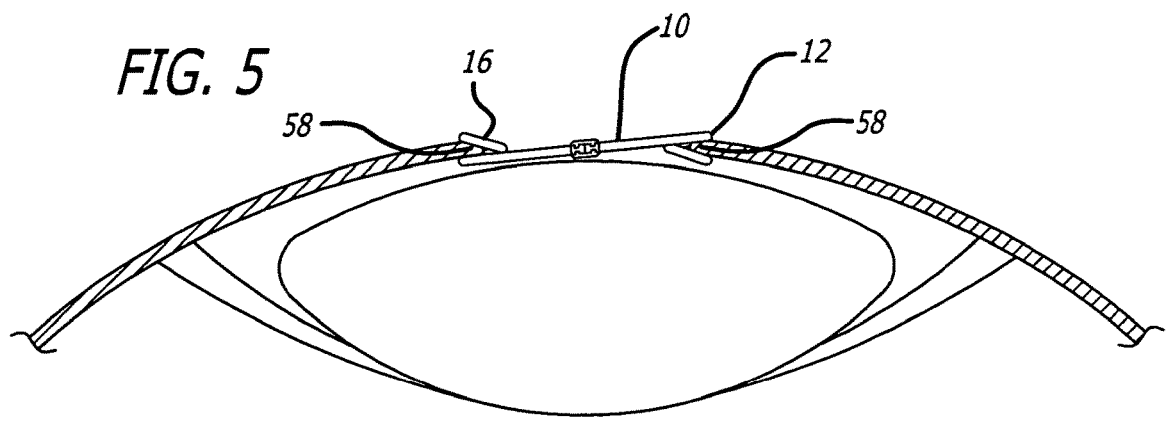
FIG. 5 is an illustration showing the iris tissue within gaps of the loops.

As shown in FIG. 1, an example of the device of the present invention is a polygonal ring formed from a single strand. As shown in FIG. 5 each loop 12, 16, etc. has a gap 58 that receives and captures iris tissue. The gap is wedge-shaped and faces the periphery of the ring 10. It is formed between a top portion of the strand and a bottom portion of the strand. The loop design provides an easy means of inserting and capturing iris tissue. The flexibility of the ring 10 allows the loops to deflect and apply a clamping force onto the iris tissue. The clamping force assists in maintaining the position of the ring relative to the eye.

Figure 6:
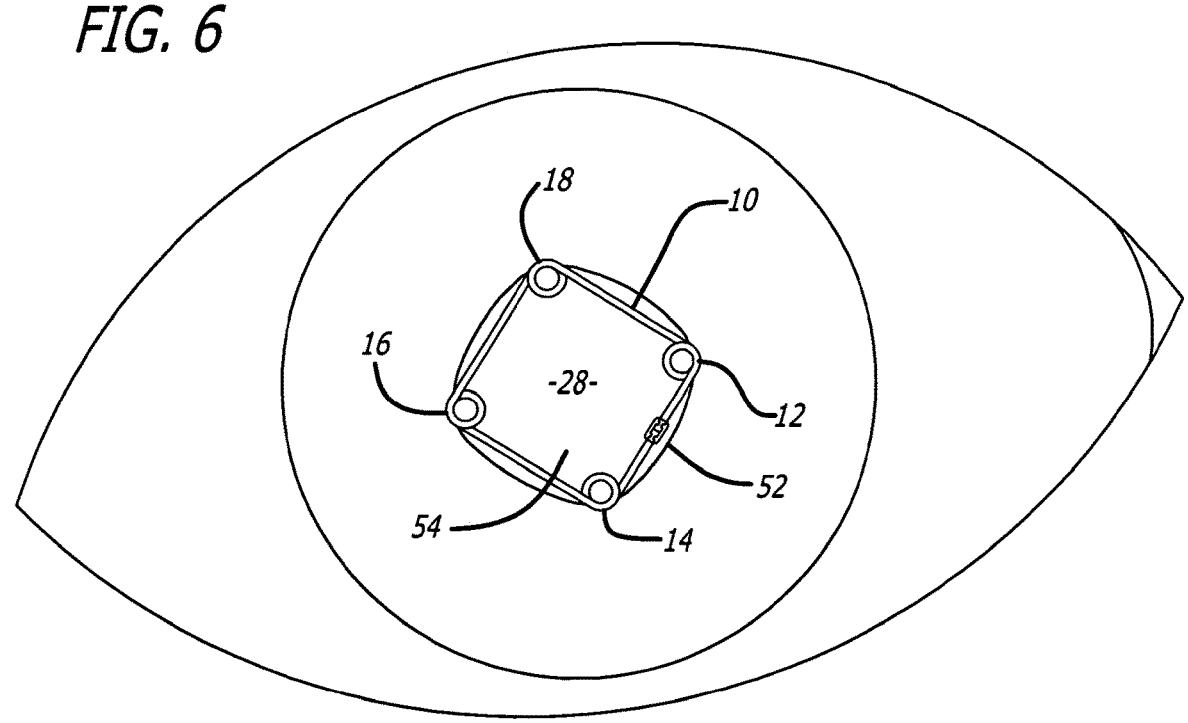
FIG. 6 is an illustration showing a pupil being maintained in an extended position by the ring.

As shown in FIG. 6 iris tissue can be inserted into the second 14 and fourth 18 loops to fully stretch the iris 52 and extend the pupil 54. An ophthalmic procedure can then be performed on the eye. For example, a phaco procedure can be performed wherein the lens is emulsified and aspirated from the eye. The ring 10 maintains the pupil 54 in the fully extended position while the center opening 28 provides a wide viewing area during the procedure. When the procedure is complete one of the sides 20, 22, 24 or 26 can be cut with an instrument and the ring 10 can be removed from the eye.

Figure 7:
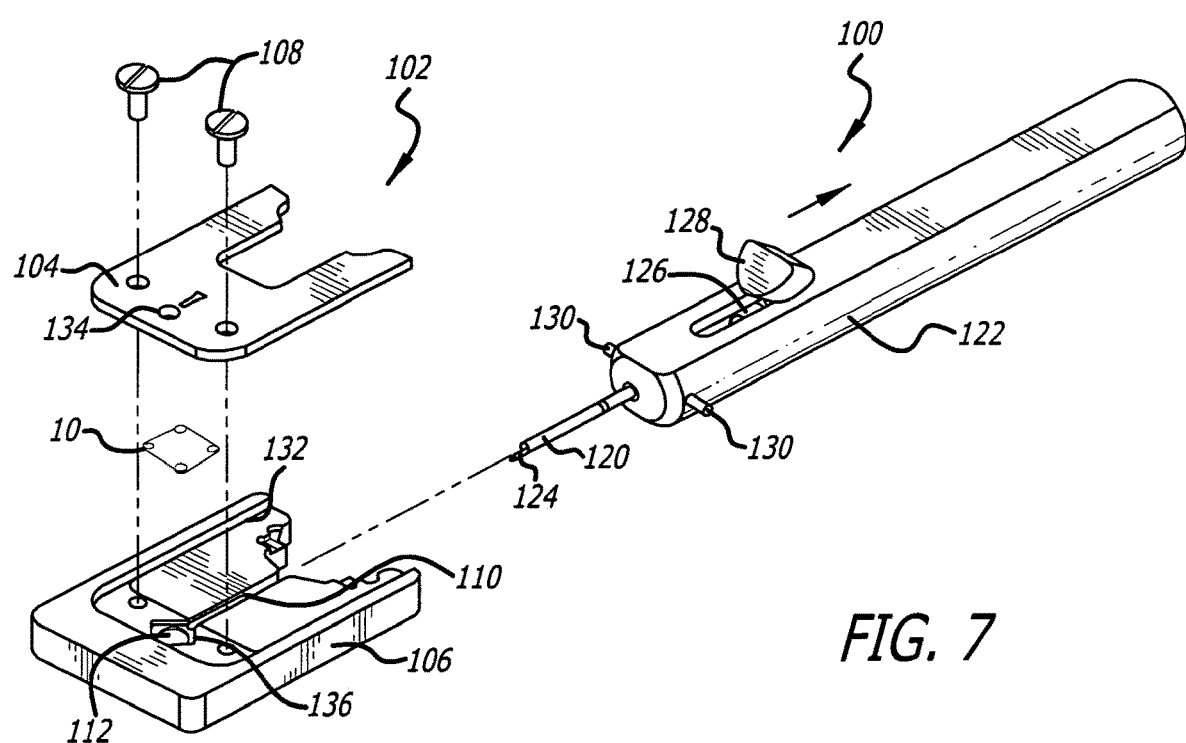
FIG. 7 is a perspective view of an injector and ring plate used to load and inject the ring.

FIG. 7 shows an embodiment of an injector 100 that can be used to inject a ring 10 into a patient's eye. The ring 10 can be loaded into the injector with the use of a ring plate 102. The ring plate 102 may include a cover 104 that is attached to a base plate 106 by fasteners 108. The base plate 106 has a channel 110 and a recess 112. The recess 112 receives the ring 10.

The injector 100 includes a cannula 120 attached to a handle 122, the handle 122 having a tapered shape configured to couple with the holder. Within the cannula 120 is a wire hook 124. The wire hook 124 is connected to an inner slide tube 126 located within the handle 122, the inner slide tube 126 having a track. A button 128 is attached to the inner slide tube 126. The injector 100 may also have a pair of guide pins 130 that are attached to the handle 122 and cooperate with corresponding channel features 132 of the base plate 106 to properly align the injector 100 when the cannula 120 is inserted into the base plate channel 110.

In operation, the cannula 120 is inserted into the base plate channel 110. When fully inserted, the wire hook 124 extends to approximately the center of the ring 10. The cover 104 may have an opening 134 that allows an operator to visually see the hook 124 within the ring opening. An operator can pull the button 128 in the direction indicated by the arrow. Pulling the button 128 causes the hook 124 to grasp the ring loops and pull the ring 10 into the cannula 120. The recess 112 has tapered walls 136 to assist in the ring collapsing within the channel 110 for insertion into the cannula 120. Once loaded, the ring 10 can be injected into a patient's eye by pushing the button 128 in the opposite direction.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An iris-expanding device injector assembly comprising:
    a handle having a first end, a second end, an interior, and a length;
    a slider coupled with the handle and configured to slide with respect to the handle;
    a cannula coupled with the first end of the handle and having an open end spaced from the first end of the handle, the cannula configured to slide in to and out from a holder containing an iris-expanding device;
    a hook connected to the slider, the hook configured to:
        extend into the holder in response to sliding the slider in a first direction;
        grasp the iris-expanding device contained in the holder, wherein the iris-expanding device is contained in the holder in an expanded configuration; and
        pull the iris-expanding device into the open end of the cannula in response to sliding the slider in a second direction,
    wherein pulling the iris-expanding device into the open end of the cannula causes the iris-expanding device to transition from the expanded configuration to a collapsed configuration in the cannula.

2. The iris-expanding device injector assembly of claim 1, wherein the cannula has a top surface and a bottom surface, and wherein the bottom surface of the cannula extends beyond the top surface of the cannula at the open end of the cannula.

3. The iris-expanding device injector assembly of claim 1, wherein the handle further comprises a top end and a bottom end, and wherein the top end comprises a groove configured to receive the slider.

4. The iris-expanding device injector assembly of claim 1, wherein the handle further comprises a first alignment pin extending from the handle in a first direction outward from the length of the cannula.

5. The iris-expanding device injector assembly of claim 4, wherein the handle further comprises a second alignment pin extending from the handle in a second direction outward from the length of the cannula.

6. The iris-expanding device injector assembly of claim 1, wherein the handle further comprises a track disposed within the interior of the handle, and wherein the slider is configured to slide along the track.

7. The iris-expanding device injector assembly of claim 1, wherein, when the iris-expanding device is in the collapsed configuration within the cannula, moving the slider in the first direction causes the hook to extend past the open end of the cannula, thereby ejecting the iris-expanding device into the expanded configuration outside of the cannula.

8. The iris-expanding device injector assembly of claim 1, wherein the first end of the handle has a tapered shape configured to couple with the holder.

9. An iris-expanding ring injector comprising:
    a handle having a distal end, a proximal end, an interior;
    a button coupled to the handle and configured to move between a first position and a second position;
    a cannula having:
        a proximal end coupled to the distal end of the handle, and
        an open distal end;
    a hook housed within the cannula when the button is in the first position,
    wherein, when the button is moved to the second position, the hook extends past the open distal end of the cannula, and is configured to grasp an iris-expanding ring in an expanded configuration, and
    wherein, when the button is moved to the first position, the iris-expanding ring grasped by the hook is transitioned from the expanded configuration into a collapsed configuration in the cannula.

10. The iris-expanding ring injector of claim 9, wherein the handle comprises a track disposed within the interior of the handle, and wherein the button is configured to slide along the track between the first position and the second position.

11. The iris-expanding ring injector of claim 9, wherein the handle further comprises a top end and a bottom end, and wherein the top end of the handle includes a groove configured to guide the button between the first position and the second position.

12. The iris-expanding ring injector of claim 9, wherein the open distal end of the cannula comprises a top surface and a bottom surface, and wherein the bottom surface of the cannula extends beyond the top surface of the cannula at the open distal end of the cannula.

13. The iris-expanding ring injector of claim 9, wherein, when the iris-expanding ring is in the collapsed configuration within the cannula, moving the button from the first position to the second position causes the hook to extend toward the open distal end of the cannula, thereby ejecting the iris-expanding ring from the cannula into the expanded configuration.

14. An iris-expanding device injector assembly comprising:
   a handle having a distal end, a proximal end, an interior, and a length;
   a slider configured to move between the distal end and the proximal end of the handle;
   a cannula having:
      a proximal end coupled to the distal end of the handle, and
      an open distal end;
   an arm having a contacting end that contacts an iris-expanding device, wherein the arm and the contacting end are housed within the cannula when the slider is in a first position towards the proximal end of the handle,
   wherein, when the arm and the contacting end are housed within the cannula, the iris-expanding device is in a collapsed configuration in the cannula, and
   wherein, when the slider is moved to a second position towards the distal end of the handle, the contacting end of the arm extends beyond the open distal end of the cannula and transfers the iris-expanding device in the collapsed configuration beyond the open distal end of the cannula into an expanded configuration.

15. The iris-expanding device injector of claim 14, wherein the interior of the handle comprises a track, and wherein the track is configured to guide the slider.

16. The iris-expanding device injector of claim 14, wherein the handle further comprises a top end and a bottom end, wherein the top end of the handle includes a groove configured to guide the slider between the distal end and the proximal end of the handle.

17. The iris-expanding device injector of claim 14, wherein the open distal end of the cannula comprises a top surface and a bottom surface, and wherein the bottom surface of the open distal end of the cannula extends beyond the top surface of the open distal end of the cannula.

18. The iris-expanding device injector assembly of claim 14, wherein the handle further comprises a first alignment pin extending from the handle in a first direction outward from the length of the cannula.

19. The iris-expanding device injector assembly of claim 18, wherein the handle further comprises a second alignment pin extending from the handle in a second direction outward from the length of the cannula.

20. The iris-expanding device injector assembly of claim 14, wherein the contacting end of the arm that contacts the iris-expanding device comprises a grasping end that grasps the iris-expanding device.

* * * * *